United States Patent
Allen et al.

(10) Patent No.: US 10,299,869 B2
(45) Date of Patent: May 28, 2019

(54) INPUT DEVICE ASSEMBLIES FOR ROBOTIC SURGICAL SYSTEMS

(71) Applicant: Covidien LP, Mansfield, MA (US)

(72) Inventors: Robert Allen, Shelton, CT (US); Chi Min Seow, New Haven, CT (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/996,048

(22) Filed: Jun. 1, 2018

(65) Prior Publication Data
US 2018/0280096 A1 Oct. 4, 2018

Related U.S. Application Data

(63) Continuation of application No. 15/116,903, filed as application No. PCT/US2015/014542 on Feb. 5, 2015, now Pat. No. 9,987,094.

(Continued)

(51) Int. Cl.
*A61B 34/30* (2016.01)
*A61B 90/00* (2016.01)
(Continued)

(52) U.S. Cl.
CPC .............. *A61B 34/30* (2016.02); *A61B 90/06* (2016.02); *G01L 3/108* (2013.01); *H02K 7/14* (2013.01);
(Continued)

(58) Field of Classification Search
CPC ... A61B 34/30; A61B 90/06; A61B 2090/064; B25J 9/18; B25J 5/00; B25J 19/02;
(Continued)

(56) References Cited

U.S. PATENT DOCUMENTS 4,620,449 A * 11/1986 Borries ............... B25B 23/1456
73/862.21
5,327,790 A * 7/1994 Levin ........................ B25J 9/12
73/862.321
(Continued)

FOREIGN PATENT DOCUMENTS

CN 102401709 A 4/2012
EP 0656500 A1 6/1995
(Continued)

OTHER PUBLICATIONS

Australian Office Action dated Nov. 1, 2018, issued in AU Appln. No. 2015214157.
(Continued)

*Primary Examiner* — Antony M Paul

(57) ABSTRACT

A reaction torque transducer for mounting a motor of an instrument drive unit includes a motor plate, a mounting plate, and a flex ring. The motor plate is fixed to the motor and the mounting plate is fixed to a fixed structure. The flex ring is positioned between the motor plate and the mounting plate. The flex ring includes a body having a first end and a second end that are moveable relative to one another. The first end of the body is fixed to the motor plate and the second end of the body is fixed to the mounting plate. The body is configured to flex in response to the first and second ends moving with respect to one another. A strain gauge is positioned on the body of the flex ring and is configured to measure flexation of the body.

20 Claims, 6 Drawing Sheets

Related U.S. Application Data

(60) Provisional application No. 61/987,893, filed on May 2, 2014, provisional application No. 61/937,044, filed on Feb. 7, 2014.

(51) Int. Cl.
  *H02P 29/00* (2016.01)
  *H02K 7/14* (2006.01)
  *G01L 3/10* (2006.01)

(52) U.S. Cl.
  CPC ........ *H02P 29/00* (2013.01); *A61B 2090/064* (2016.02)

(58) Field of Classification Search
  CPC ......... G05B 19/19; G01L 3/108; H02P 29/00; H02P 3/00; H02P 6/00; H02P 21/00; H02P 41/00; H02K 7/14
  USPC .............. 318/568.11, 568.12, 568.16, 568.2, 318/400.14, 432, 400.01; 901/8, 10, 19, 901/23, 30; 606/130
  See application file for complete search history.

(56) References Cited

U.S. PATENT DOCUMENTS

| | | | |
|---|---|---|---|
| 5,533,410 A | 7/1996 | Smith | |
| 5,792,135 A | 8/1998 | Madhani et al. | |
| 8,161,827 B2* | 4/2012 | Kato | G01L 3/1457 73/862.044 |
| 8,281,670 B2 | 10/2012 | Larkin et al. | |
| 8,359,932 B2 | 1/2013 | Eriksen et al. | |
| 8,726,741 B2* | 5/2014 | Krippner | G01L 3/1457 73/862.045 |
| 9,561,585 B2* | 2/2017 | Tanaka | B25J 9/06 |
| 9,739,674 B2* | 8/2017 | Malackowski | G01L 5/226 |
| 9,987,094 B2 | 6/2018 | Allen et al. | |
| 2007/0129846 A1 | 6/2007 | Birkenbach et al. | |
| 2010/0005907 A1 | 1/2010 | Kato et al. | |
| 2011/0314935 A1 | 12/2011 | Krippner et al. | |
| 2012/0048628 A1* | 3/2012 | Kawanami | B25J 9/0003 180/21 |
| 2012/0116416 A1 | 5/2012 | Neff et al. | |
| 2013/0317519 A1 | 11/2013 | Romo et al. | |
| 2014/0060223 A1 | 3/2014 | Tanaka | |

FOREIGN PATENT DOCUMENTS

| | | |
|---|---|---|
| JP | 55006268 | 1/1980 |
| JP | 2003083824 A | 3/2003 |
| JP | 2009058388 A | 3/2009 |
| JP | 2012047460 A | 3/2012 |
| WO | 2012165068 A1 | 12/2012 |

OTHER PUBLICATIONS

European Search Report dated Oct. 30, 2017, issued in EP Appln. No. 15746311.

Chinese Office Action dated May 28, 2018 issued in CN Appln. No. 2015800075513.

International Search Report for (PCT/US2015/014542) date of completion is May 14, 2015 (3 pages).

Japanese Office Action dated Oct. 15, 2018, issued in JP Appln. No. 2016544516.

* cited by examiner

INPUT DEVICE ASSEMBLIES FOR ROBOTIC SURGICAL SYSTEMS

CROSS-REFERENCE TO RELATED APPLICATIONS

This application is a continuation of U.S. patent application Ser. No. 15/116,903, filed Aug. 5, 2016, which is a U.S. National Stage Application filed under 35 U.S.C. § 371(a) of International Patent Application Serial No. PCT/US2015/014542, filed Feb. 5, 2015, which claims the benefit of, and priority to, each of U.S. Provisional Patent Application Ser. No. 61/937,044, filed Feb. 7, 2014, and U.S. Provisional Patent Application Ser. No. 61/987,893, filed May 2, 2014. The entire contents of each of the above applications are hereby incorporated by reference.

BACKGROUND

Robotic surgical systems have been used in minimally invasive medical procedures. During such a medical procedure, the robotic surgical system is controlled by a surgeon interfacing with a user interface. The user interface allows the surgeon to manipulate an end effector that acts on a patient. The user interface includes an input controller or handle that is moveable by the surgeon to control the robotic surgical system.

The end effectors of the robotic surgical system are positioned at the end of robotic arms. Each end effector is manipulated by an Instrument Drive Unit (IDU). The IDU includes a drive motor that is associated with the end effector to move the end effector about a respective axis or to perform a particular function of the end effector (e.g., approximate, pivot, etc. jaws of the end effector). The IDU can include a plurality of drive motors with each drive motor being associated with a respective degree of freedom or function of the end effector.

There is a need for precisely and accurately measuring the force applied by the drive motors in order to anticipate and predict a life expectancy of the drive motors. In addition, there is a continuing need for reduced feedback signal response time for providing real-time haptic feedback to a user.

SUMMARY

In an aspect of the present disclosure, a torque transducer for mounting a motor includes a motor plate, a mounting plate, a flex ring, and a strain gauge. The motor plate is configured to be fixed to the motor and the mounting plate is configured to be fixed to fixed structure. The flex ring is positioned between the motor plate and the mounting plate. The flex ring includes a body having first and second ends that are moveable relative to one another. The first end of the body is fixed to the motor plate and the second end of the body is fixed to the mounting plate. The body is configured to flex in response to the first and second ends moving with respect to one another. The strain gauge is positioned on the body of the flex ring to measure flexation of the body.

In aspects, the torque transducer includes a bearing that has an inner surface positioned over the motor plate and an outer surface positioned within the mounting plate. The motor plate may include a bearing stem that extends towards the mounting plate. The inner surface of the bearing may be fixed to the bearing stem. The mounting plate may include a bearing cylinder that extends towards the motor plate. The outer surface of the bearing may be fixed to an inner surface of the bearing cylinder. The flex ring may be positioned over an outer surface of the bearing cylinder and/or the bearing.

In some aspects, the motor plate includes a radially extending motor flange and the mounting plate includes a radially extending mounting flange. The flex ring may include a radially extending first flange at the first end of the body and a radially extending second flange at the second end of the body. The first flange may be fixed to the motor flange and the second flange may be fixed to the mounting flange.

In certain aspects, the body of the flex ring includes a low strain member and a high strain member that each have a first end fixed to the motor ring and a second end fixed to the mounting ring. Each of the low and high strain members are parallel to a longitudinal axis that is defined between centers of the motor and mounting rings. The mounting ring may define recesses that clock the mounting ring to the fixed structure.

In particular aspects, the body of the flex ring has inner and outer diameters that determine a stiffness of the body. The strain gauge may be positioned halfway between the first and second end of the body of the flex ring.

In another aspect of the present disclosure, a drive unit includes a fixed structure, a first motor, and a first torque transducer. The first motor has a drive shaft that passes through the fixed structure. The first torque transducer is positioned between the fixed structure and the first motor about the drive shaft of the first motor to mount the first motor to the fixed structure. The first torque transducer includes a motor plate, a mounting plate, a flex ring, and a strain gauge. The motor plate is positioned about the drive shaft of the first motor and is fixed to the first motor. The mounting plate is positioned about the drive shaft of the first motor and is fixed to the fixed structure. The flex ring is positioned between the motor plate and the mounting plate and about the drive shaft of the first motor. The flex ring includes a body that has first and second ends that are moveable relative to one another. The first end of the body is fixed to the motor plate and the second end of the body is fixed to the mounting plate. The body is configured to flex in response to the first and second ends moving with respect to one another. The strain gauge is positioned on the body of the flex ring to measure flexation of the body.

In aspects, the drive unit includes a first drive cable that is operably associated with the drive shaft and is configured to manipulate a tool in response to rotation of the drive shaft. The drive unit may include a converter that is coupled to the drive shaft of the motor to convert rotation of the drive shaft into linear movement of the first drive cable.

In some aspects, the first motor is configured to manipulate a tool in a first degree of freedom. The drive unit may include a second motor that is configured to manipulate the tool in a second degree of freedom different from the first degree of freedom. The second motor may be mounted to the fixed structure by a second torque transducer.

In certain aspects, the fixed structure is an end of an arm of a robotic system.

In another aspect of the present disclosure, a method of measuring a force exerted by a tool includes activating a motor of a drive unit to manipulate the tool and measuring a reaction torque of the motor in response to activating the motor. The motor is mounted to a fixed structure of the drive unit by a torque transducer and is operatively associated with the tool to manipulate the tool. Measuring the reaction torque of the motor includes measuring flexation of a body of a flex ring of the torque transducer.

In some aspects, activating the motor of the drive unit includes supplying energy to the motor. The method may include adjusting energy supplied to the motor in response to the measured reaction torque of the motor.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
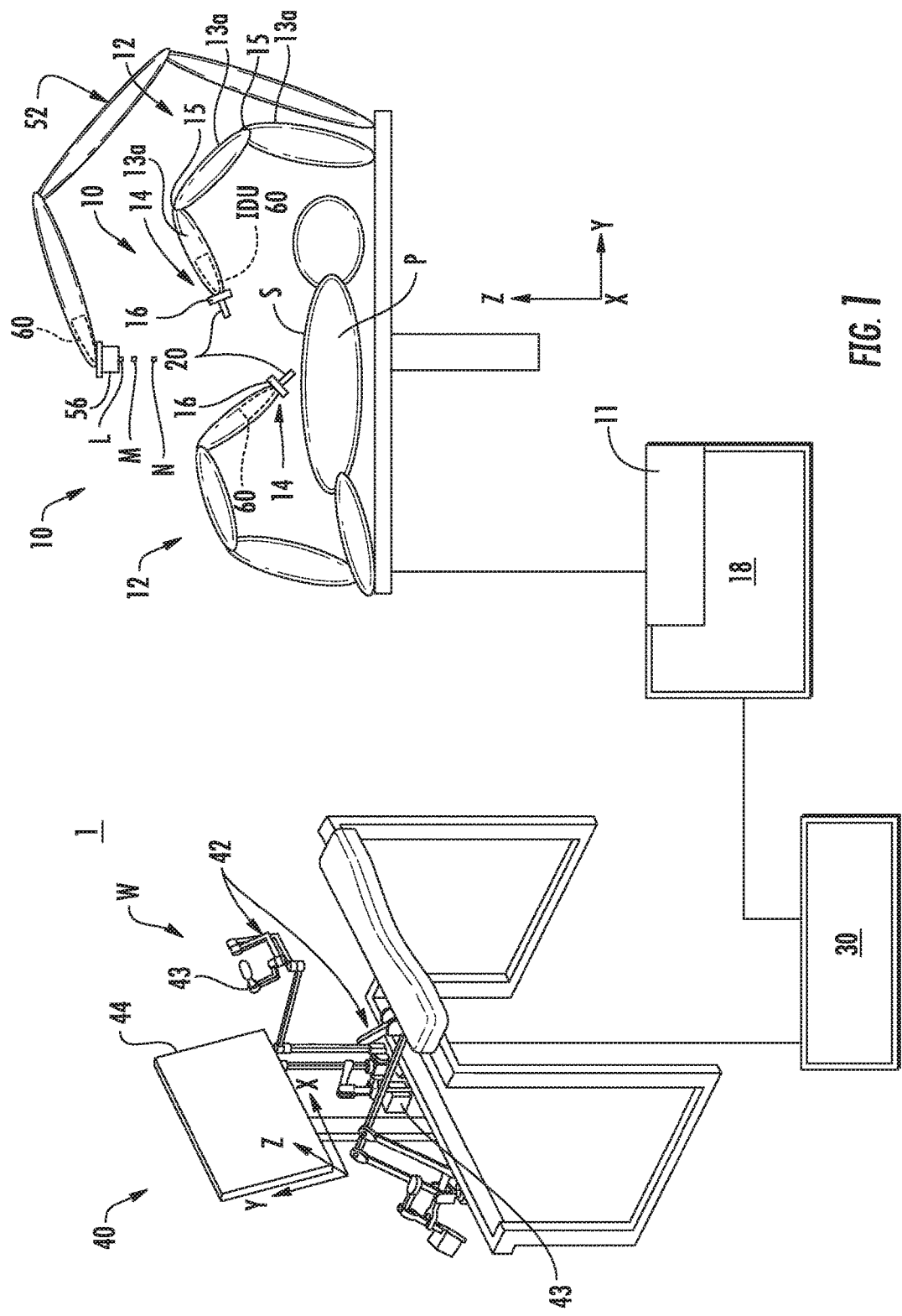
FIG. 1 is a schematic illustration of a user interface and a robotic system.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

The present disclosure generally relates to a torque transducer that measures the reaction torque of a motor of an instrument drive unit (IDU) to determine the forces being applied to an end effector of a robotic surgical system. The torque transducer is positioned between the motor and a fixed plate of the IDU to secure the motor within the IDU. The measured reaction torque may be used to control the end effector and/or provide feedback to the user of the robotic surgical system.

Referring to FIG. 1, a robotic surgical system 1 is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms each having a plurality of members 13. A member 13a of the plurality of members 13 has an end 14 that supports an end effector or tool 20 which is configured to act on tissue. In addition, the end 14 of the member 13a may include an imaging device 16 for imaging a surgical site "S". Each of the plurality of members 13 of the linkages 12 may be connected to one another about joints 15. The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the end 14 of the member 13a and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 42 which allow a clinician to manipulate the robotic system 10 (e.g., move the linkages 12, the ends 14 of the linkages 12, and/or the tools 20). Each of the input handles 42 is in communication with the processing unit 30 to transmit control signals thereto and to receive feedback signals therefrom. Each of the input handles 42 may include input devices which allow the surgeon to manipulate (e.g., clamp, grasp, fire, open, close, rotate, thrust, slice, etc.) the tools 20 supported at the end 14 of the member 13a.

For a detailed discussion of the construction and operation of a robotic surgical system 1, reference may be made to U.S. Patent Publication No. 2012/0116416, entitled "Medical Workstation", the entire contents of which are incorporated herein by reference.

Figure 2:
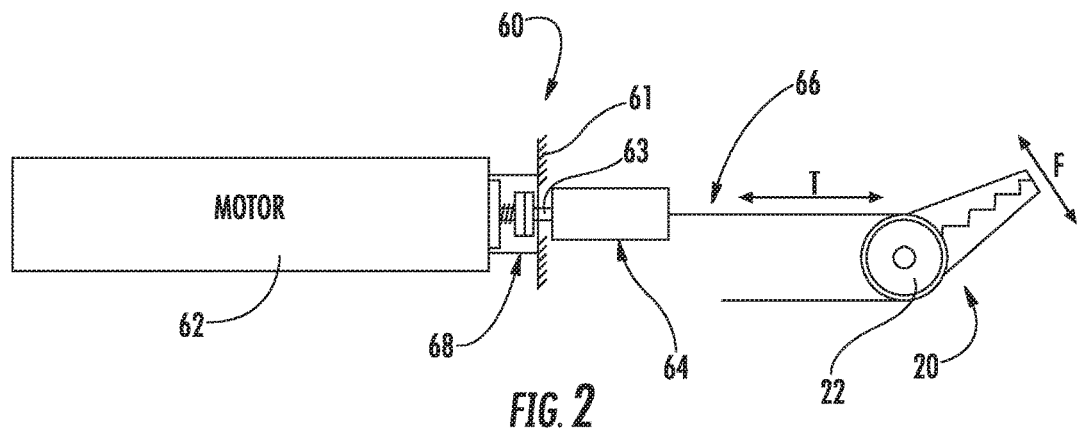
FIG. 2 is a schematic illustration of a motor of an IDU of FIG. 1 associated with an end effector of FIG. 1.

Referring also to FIG. 2, an instrument drive unit (IDU) 60 is disposed within or supported on the member 13a adjacent the end 14. The IDU 60 is operatively associated to a tool 20 coupled to the end 14 to manipulate the tool 20 in response to control signals transmitted from the processing unit 30. The IDU 60 includes at least one motor 62, a respective converter 64, a respective drive cable 66, and a respective torque transducer 68. The motor 62 rotates a drive shaft 63 that extends through the torque transducer 68 in response to energy being supplied to the motor 62. The converter 64 converts rotation of the drive shaft 63 of the motor 62 to linear movement of the drive cable 66 as indicated by arrow "T". The converter 64 may be secured to a fixed plate 61 of the IDU 60.

The drive cable 66 extends from the converter 64 to the end effector 20. As shown in FIG. 2, the drive cable 66 is associated with effecting a rotation of the end effector 20 about a pulley 22. It will be appreciated each IDU 60 may include a plurality of motors 62 with a drive cable 66 associated with each of the plurality of motors 62 such that each drive cable 66 is associated with a different degree of freedom of the end effector 20 or a function of the end effector 20.

Figure 3:
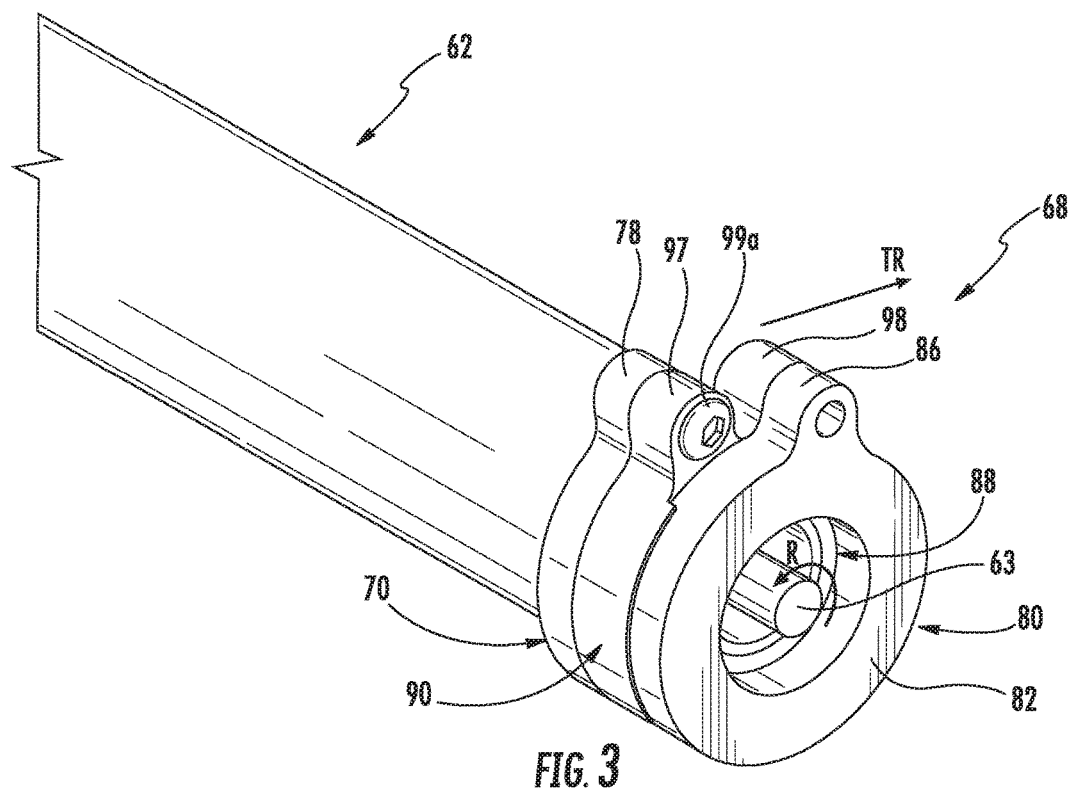
FIG. 3 is a perspective view of a torque transducer of the IDU of FIG. 2 in accordance with the present disclosure.
Figure 4:
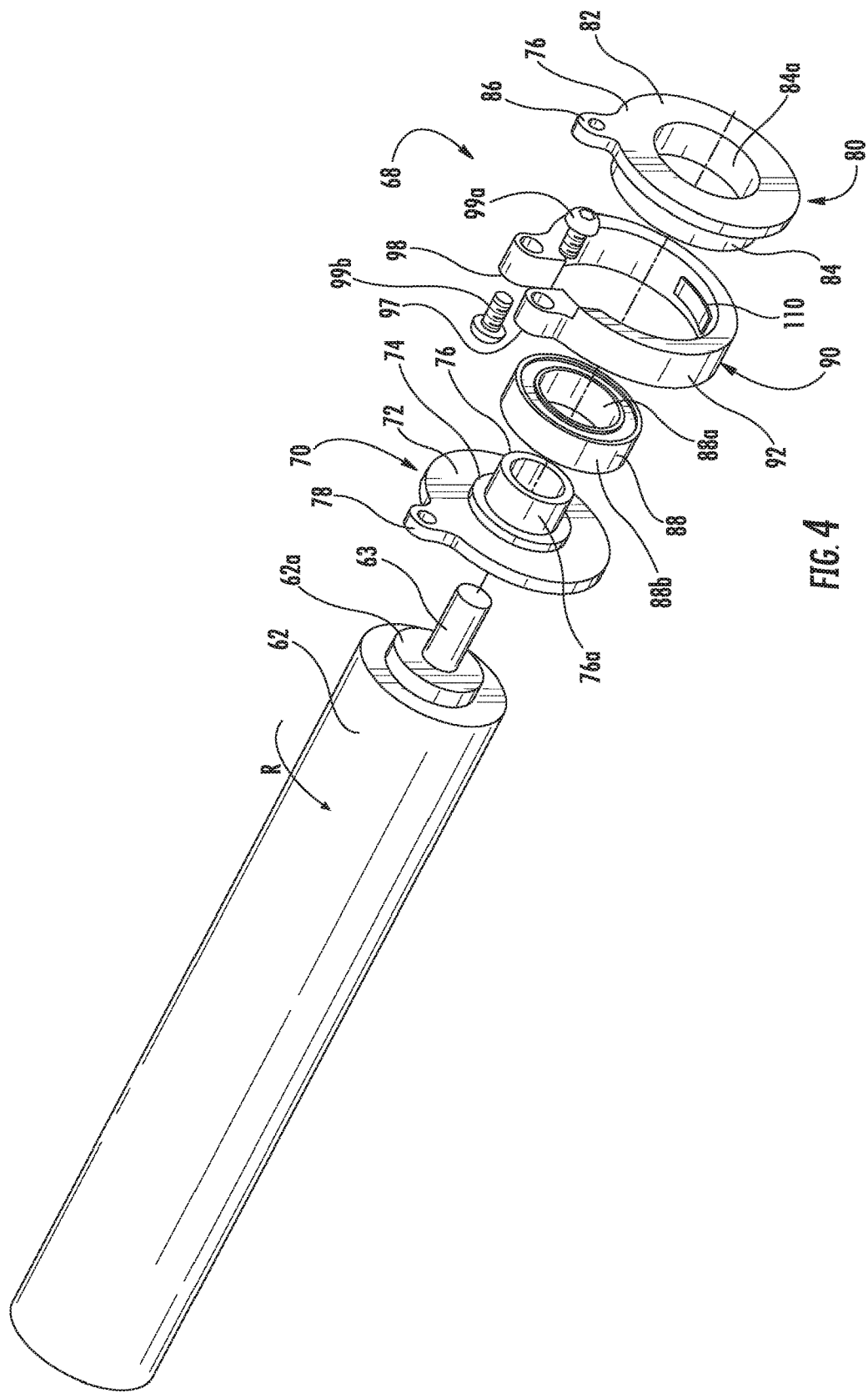
FIG. 4 is an exploded perspective view, with parts separated, of the torque transducer of FIG. 3.

With reference to FIGS. 2-4, the torque transducer 68 is provided in accordance with the present disclosure and is a reaction torque transducer that measures motor torque applied by the motor 62 to the converter 64 and thus, measures force applied to the end effector 20 by the cable 66. The torque transducer 68 is positioned about the drive shaft 63 of the motor 62 and secures the motor 62 to the fixed plate 61 of the IDU 60. The torque transducer 68 includes a motor plate 70, a mounting plate 80, a bearing 88, a flex ring 90, and a strain gauge 110 (FIG. 4).

The motor plate 70 is rotatably supported on the motor 62 about the drive shaft 63. The motor plate 70 includes a cylindrical body 72 that defines a recess or bore 74 facing the motor 62 which is dimensioned to receive a protrusion 62a of the motor 62 extending about the drive shaft 63. The motor plate 70 is press-fit over the protrusion 62a of the motor 62 such that the protrusion 62a of the motor 62 is received within the recess 74 in an interference fit. In embodiments, the protrusion 62a of the motor 62 may have a geometric shape (e.g., square, pentagonal, etc.) and that the recess 74 of the motor plate 70 may have a complimentary geometric shape to receive the protrusion 62 to rotatably fix the motor plate 70 to the motor 62. In such embodiments, a press-fit between the body 72 of the motor plate and the protrusion 62a of the motor is not required. The body 72 of the motor plate 70 includes a bearing stem 76 that extends from a face of the body 72 facing away from the motor 62. The bearing stem 76 includes an outer surface 76a that is configured to support an inner race or surface 88a of the bearing 88. The inner surface 88a of the bearing 88 may be press-fit over the bearing stem 76 of the motor plate 70. The motor plate 70 also includes a flange or ear 78 that extends radially from an outer surface of the body 72.

The mounting plate 80 is positioned between the motor plate 70 and the fixed plate 61 of the IDU 60 (FIG. 2). The mounting plate 80 includes a body 82 that is secured to the fixed plate 61 to rotatably and longitudinally fix the mounting plate 80 relative to the fixed plate 61. It is contemplated that the mounting plate 76 may be integrally formed with the fixed plate 61, welded to the fixed plate 61, affixed to the fixed plate 61, or any combination thereof. The body 82 includes a bearing cylinder 84 that extends towards the motor plate 70. The bearing cylinder 84 includes an inner surface 84a that is dimensioned to receive an outer race or surface 88b of the bearing 88. The outer race 88b of the bearing 88 may be press-fit into the bearing cylinder 84. The bearing 88 has a length along a longitudinal axis of the drive shaft 63 such that the bearing 88 is disposed within the bearing cylinder 84 of the mounting plate 80 and over the bearing stem 76 of the motor plate 70. The mounting plate 80 also includes a flange or ear 86 extending radially from the body 82.

Figure 5:
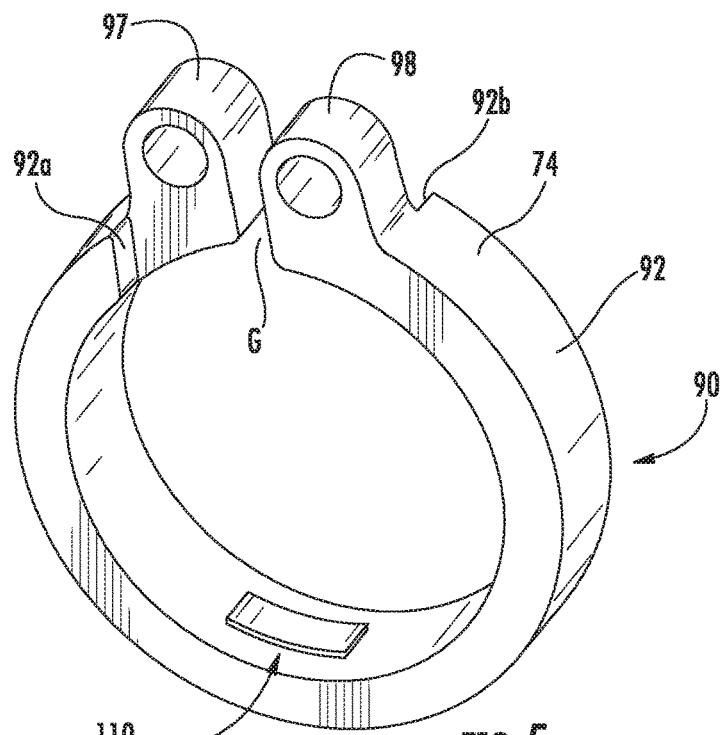
FIG. 5 is a perspective view of a flex ring of the torque transducer of FIG. 4.
Figure 6:
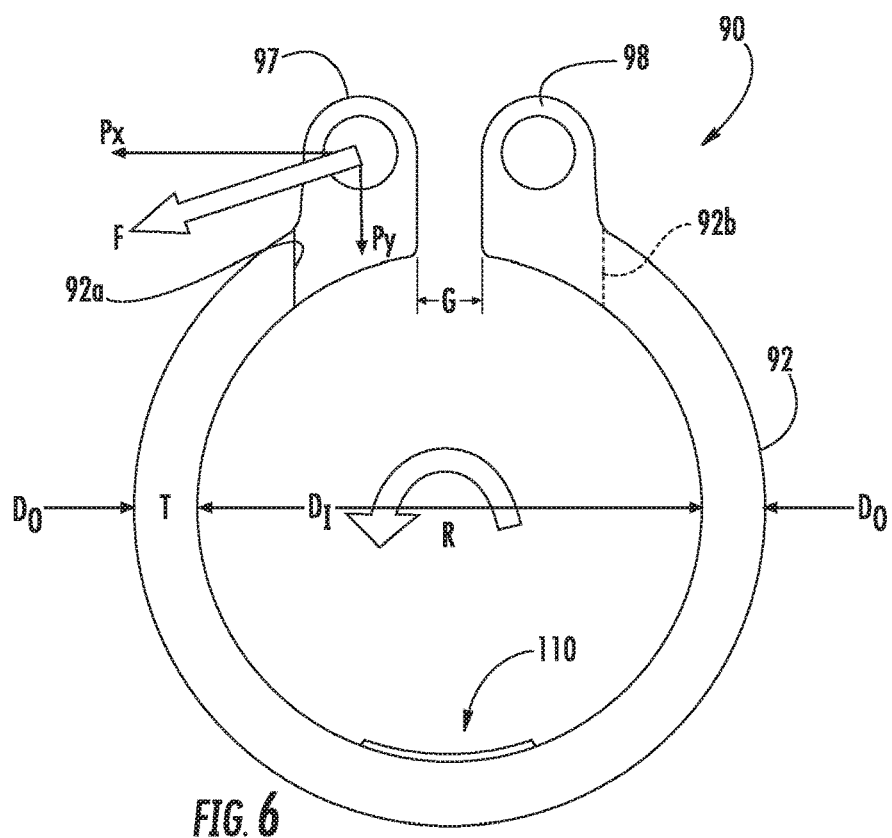
FIG. 6 is an end view of the flex ring of the torque transducer of FIG. 4.

Referring to FIGS. 4-6, the flex ring 90 is an open ring positioned between the motor plate 70 and the mounting plate 80 over the bearing cylinder 84 of the mounting plate 80. The flex ring 90 includes a body 92 that has an inner diameter $D_I$ larger than the bearing cylinder 84 of the mounting plate 80 such that the body 92 does not contact the bearing cylinder 84. The body 92 of the flex ring 90 has first and second ends 92a, 92b that are moveable relative to one another in a plane transverse to the longitudinal axis of the drive shaft 63 or substantially tangentially to the longitudinal axis of the drive shaft 63. The first end 92a of the body 92 includes a motor flange 97 and the second end 92b of the body 92 includes a mounting flange 98 that define a gap "G" therebetween. The flanges 97, 98 extend radially from the body 92 of the flex ring 90 and have a length or thickness along the longitudinal axis of the drive shaft 63 that is less than the length or thickness of the body 92.

The motor flange 97 is aligned with a surface of the body 92 facing the motor plate 70 such that the surface of the body 92 facing the motor plate 70 is continuous with the motor flange 97. The mounting flange 98 is aligned with a surface of the body 92 facing the mounting plate 80 such that the surface of the body 92 facing mounting plate 80 is continuous with the mounting flange 98. The first end 92a of the body 92 may form a notch with the motor flange 97 that engages a corresponding notch of the mounting plate 80 to limit the movement of the motor flange 97 towards the mounting flange 98, as shown in FIG. 3. Similarly the second end 92b of the body 92 may form a notch with the mounting flange 98 that engages a corresponding notch of the motor plate 70 to limit movement of the motor flange 97 towards the mounting flange 98.

With particular reference to FIG. 4, a first fastener 99a passes through the motor flange 97 of the flex ring 90 and the flange 78 of the motor plate 70 to rotatably fix the motor flange 97, and thus the first end 92a of the body 92, to the motor 62. A second fastener 99b passes through the mounting flange 98 of the flex ring 90 and the flange 86 of the mounting plate 80 to rotatably fix the mounting flange 98, and thus the second end 92b of the body 92, to the fixed plate 61. The fastener 99b may pass through the flange 86 of the mounting plate 80 and into the fixed plate 61.

Briefly referring back to FIG. 3, when the motor 62 is energized to rotate the drive shaft 63 in a first direction as indicated by arrow R, the motor 62 is subject to a reactive torque from the drive shaft 63 in a second direction opposite the first direction. This reactive torque passes through the torque transducer 68 which secures the motor 62 to the fixed plate 61. As the reactive torque passes through the torque transducer 68, the body 92 of the flex ring 90 flexes such that the first and second ends 92a, 92b move relative to one another. The flex of the body 92 is measured by a strain gauge 110 (FIG. 6) positioned on an inner surface of the body 92 opposite of the gap G. The configuration of the motor plate 70, the mounting plate 80, the bearing 88, and the flex ring 90 isolate the body 92 of the flex ring 90 from flexing in a direction other than the opening or closing the gap G. As detailed below, the gap G opens and closes in response to the reaction torque of the motor 62.

Referring to FIGS. 5 and 6, the strain gauge 110 is positioned opposite the gap "G" between the first and second ends 92a, 92b at a point of maximum flexation of the body 92. The flex ring 90 is tuned to the application of the motor 62 to provide adequate stiffness to prevent excessive displacement or flexation of the body 92 and to provide enough flexation of the body 92 for a measurable response from the strain gauge 110. Excessive flexation of the flex ring 90 may result in lost motion of the end effector 20. However, insufficient flexation of the body 92 will result in an undetectable flexation of the body 92 (i.e., the noise of the system may be greater than the measurable flexation).

The flexation of the body 92 of the flex ring 90 is tuned to a particular application of the motor 62 by varying the inner diameter "$D_I$" and an outer diameter "$D_O$" of the body 92 to increase or decrease a thickness "T" of the body 92. It will be appreciated that as the thickness "T" of the body 92 of the flex ring 90 is increased, the stiffness of the body 92 is increased and the flexation is decreased when the body 92 is subjected to the same torque. Likewise, as the thickness "T" of the body 92 of the flex ring 90 is decreased, the stiffness of the body 92 is decreased and the flexation is increased when the body 92 is subjected to the same torque. The flex ring 90 may also be tuned by varying the material of the flex ring 90 (e.g., steel, aluminum, plastic, etc.). Further, it will be appreciated that as the inner diameter "$D_I$" and the outer diameter "$D_O$" of the body 92 are increased, with the thickness "T" remaining constant, the stiffness of the body 92 is increased.

Figure 7:
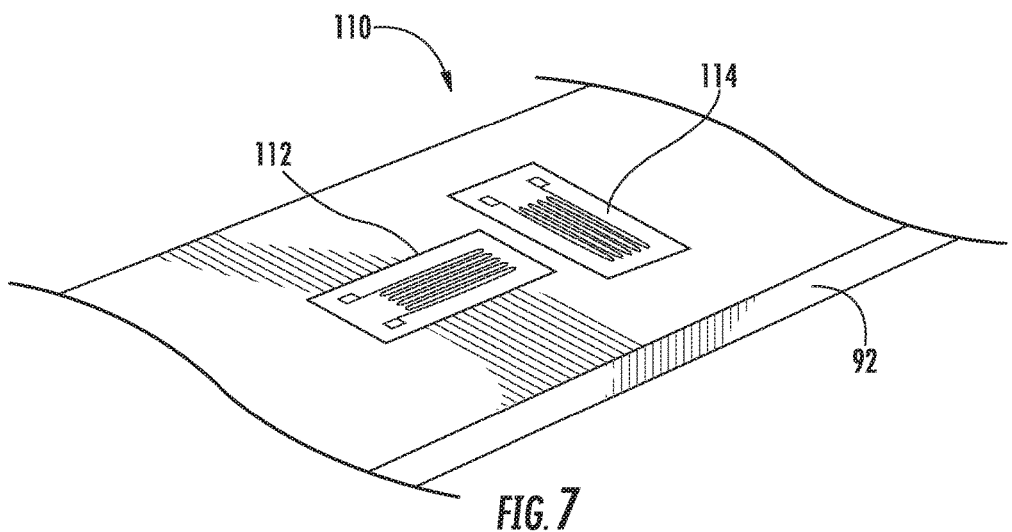
FIG. 7 is a schematic view of a strain gauge on the flex ring of FIG. 5.

Referring to FIG. 7, the strain gauge 110 includes an active strain sensor 112 and a calibration strain sensor 114.

The active strain sensor 112 is aligned with a direction of the flexation of the body 92, e.g., in a direction transverse to the longitudinal axis of the drive shaft 63 (FIG. 4). The active strain sensor 112 measures the strain of the body 92 of the flex ring 90 as the body 92 flexes in response to reactive torque of the motor 62. The calibration strain sensor 114 is aligned with the longitudinal axis of the drive shaft 63 and is orthogonal to the active strain sensor 112. The calibration strain sensor 114 measures strain of the body 92 of the flex ring 90 due to factors other than the flexation of the body 92 in response to reactive torque of the motor 62 (e.g., thermal expansion of the body 92).

Figure 8:
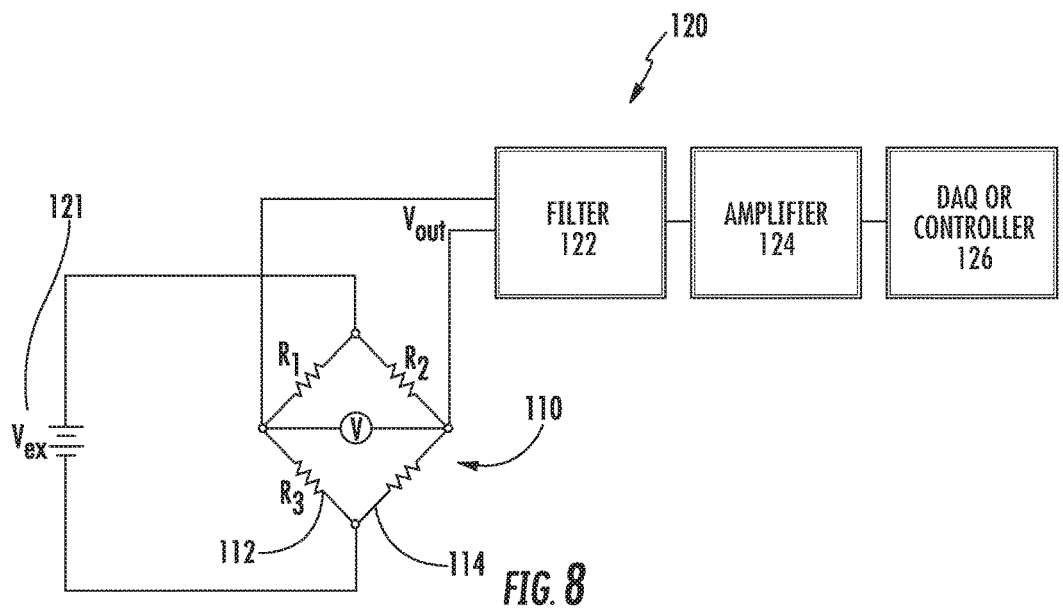
FIG. 8 is a schematic view of a sensor circuit of the strain gauge of FIG. 7.

With reference to FIG. 8, a measurement circuit 120 determines the reaction torque of the motor 62 from the measured flexation from the strain gauge 110. The measurement circuit 120 includes the strain gauge 110, a voltage source 121, a filter 122, an amplifier 124, and a controller 126. The strain gauge 110 includes the active strain sensor 112 and the calibration strain sensor 114 as part of a bridge circuit including two resistors $R_1$, $R_2$. Strain of the body 92 of the flex ring 90 is measured as a voltage change of the strain gauge 110 whereby the resistance of each of the strain sensors 112, 114 varies in response to flexation of the body 92. The measured voltage is passed from strain gauge 110 to a filter 122. As shown, the measured voltage accounts for factors other than the flexation of the body 92 as a result of positioning the calibration strain sensor 114 adjacent and orthogonal to the active strain sensor 112. The filter 122 is a low pass filter to remove noise from the measured voltage. The filter 122 transmits the filtered voltage to an amplifier 124 which transmits the amplified voltage to a controller 126. The controller 126 detects changes in the amplified voltage and calculates a strain of the body 92 of the flex ring 90. From the strain of the body 92 of the flex ring 90, the controller 126 calculates the flexation of the body 92. The controller 126 calculates reaction torque of the motor 62 from the flexation of the body 92 of the flex ring 90 in view of the known properties and dimensions of the body 92. The controller 126 transmits the calculated reaction torque of the motor 62 to the processor 30 (FIG. 1).

The processor 30 analyzes the reaction torque of the motor 62 to determine the force applied to the end effector 20 by the IDU 60. The processor 30 may adjust energy supplied to the motor 62 in response to the force applied to the end effector 20. Additionally or alternatively, the processor 30 may provide feedback to a user through the user interface 40 in response to the reaction torque of the motor 62. The feedback may be visual, audible, or haptic.

It is also contemplated that the robot system 10 may include a drive unit 11 (FIG. 1) positioned in the robot base 18 that is operatively associated with the linkages 12 to move the plurality of members 13 about the joints 15 in response to input from a user. The drive unit 11 may include a torque transducer (not shown) similar to torque transducer 68 to measure torque applied to the linkages 12 by the drive unit 11.

Figure 9:
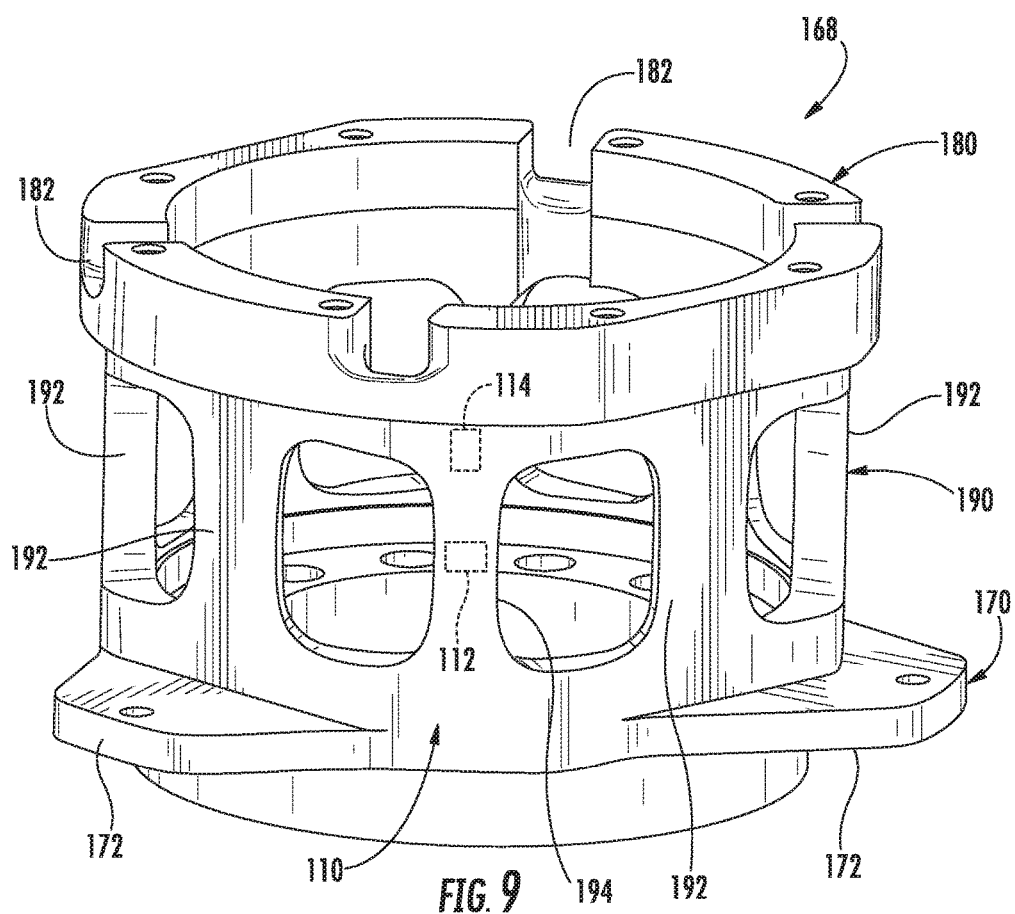
FIG. 9 is another torque transducer in accordance with the present disclosure that is mountable to the motor of FIG. 2.

Referring now to FIG. 9, a torque transducer 168 is provided in accordance with the present disclosure and includes a motor ring or plate 170, a mounting ring or plate 180, and a flex ring 190 positioned between the motor and mounting rings 170, 180. The torque transducer 168 is positioned over a drive shaft of a motor (e.g., drive shaft 63 of a motor 62 (FIG. 3)) and supports the motor 62 to a fixed plate (e.g., fixed plate 61 (FIG. 2)) of an IDU. The motor ring 170 is secured to a motor 62 by flanges 172 to rotatably fix the motor 62 to the motor ring 170. The mounting ring 180 is secured to a fixed plate or structural member (not shown). The mounting ring 180 defines clocking recesses 182 that are configured to engage the fixed plate to rotatably fix the mounting ring 180 to the fixed plate.

The flex ring 190 includes low strain members 192 and a high strain member 194 extending between the motor and mounting rings 170, 180. The low and high strain members 192, 194 are parallel to the longitudinal axis of a driveshaft of a motor (e.g., drive shaft 63 of motor 62 (FIG. 3)) with a first end of each of the low and high strain members 192, 194 fixed to the motor ring 170 and a second end of each of the low and high strain members 192, 194 fixed to the mounting ring 180. The strain gauge 110 is disposed on the high strain member 194 with the active strain sensor 112 positioned on a portion of the high strain member 194 subject to a maximum flexation as the torque transducer 168 is torqued. The calibration strain sensor 114 is positioned on a portion of the high strain member 192 that is subject to no or minimum flexation as the torque transducer 168 is torqued. As shown, the active strain sensor 112 is positioned on the high strain member 194 halfway between the motor and mounting rings 170, 180 and orientated in perpendicular to the longitudinal axis of the driveshaft of the motor. The calibration strain sensor 114 is positioned adjacent the mounting ring 180 and orientated parallel to the longitudinal axis of the drive shaft of the motor. It will be appreciated that the calibration strain sensor 114 is orientated orthogonal to the active strain sensor 112.

The flex ring 190 functions in a manner similar to flex ring 90 in response to the reaction torque of the motor and the strain gauge 110 measures the flexation of the high strain member 194 of the flex ring 190 to calculate the reaction torque of the motor in a similar manner.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A torque transducer for mounting a motor, comprising:
   a motor plate configured to be fixed to the motor;
   a mounting plate configured to be fixed to a fixed structure; and
   a flex ring interconnecting the motor plate and the mounting plate, the flex ring including:
   a first member having a first portion fixed to the motor plate and a second portion fixed to the mounting plate;
   a second member having a first segment fixed to the motor plate and a second segment fixed to the mounting plate; and
   an active strain gauge positioned on the first member between the first and second portions, the active strain gauge configured to measure flexation of the first member in response to the first portion moving relative to the second portion.

2. The torque transducer according to claim 1, wherein the first member is configured as a relatively high strain member and the second member is configured as a relatively low strain member.

3. The torque transducer according to claim 1, wherein the first member has a region of relatively maximum flexation between the first and second portions, the active strain gauge positioned on the region of relatively maximum flexation.

4. The torque transducer according to claim 1, wherein the flex ring includes a calibration strain gauge, the calibration strain gauge positioned on a region of the flex ring configured to minimize flexation, the calibration strain gauge configured to account for environmental strain.

5. The torque transducer according to claim 4, wherein the calibration strain gauge is disposed on the first portion of the first member.

6. The torque transducer according to claim 1, wherein the active strain gauge is oriented to measure strain in a direction transverse to a longitudinal axis of the first member.

7. The torque transducer according to claim 1, wherein the motor plate includes a radially extending motor flange configured to fix the motor plate to the motor.

8. The torque transducer according to claim 1, wherein the mounting plate defines a clocking recess configured to clock the mounting ring to the fixed structure.

9. An drive unit comprising:
a fixed structure;
a first motor having a drive shaft passing through the fixed structure; and
a first torque transducer mounting the first motor to the fixed structure, the first torque transducer including:
a motor plate fixed to the first motor;
a mounting plate fixed to fixed structure; and
a flex ring interconnecting the motor plate and the mounting plate, the flex ring including:
a first member having a first portion fixed to the motor plate and a second portion fixed to the mounting plate;
a second member having a first segment fixed to the motor plate and a second segment fixed to the mounting plate; and
an active strain gauge positioned on the first member between the first and second portions, the active strain gauge configured to measure flexation of the first member in response to the first portion moving relative to the second portion.

10. The drive unit according to claim 9, further comprising a first drive cable operably associated with the drive shaft and configured to manipulate a tool in response to rotation of the drive shaft.

11. The drive unit according to claim 10, further comprising a converter coupled to the drive shaft of the first motor to convert rotation of the drive shaft into linear movement of the first drive cable.

12. The drive unit according to claim 11, wherein the first motor is configured to manipulate a tool in a first degree of freedom.

13. The drive unit according to claim 12, further comprising a second motor configured to manipulate the tool in a second degree of freedom different from the first degree of freedom, the second motor mounted to the fixed structure by a second torque transducer.

14. The drive unit according to claim 9, wherein the fixed structure is an end of an arm of a robotic system.

15. A torque transducer for mounting a motor, comprising:
a motor ring configured to be fixed to the motor;
a mounting ring configured to be fixed to a fixed structure; and
a flex ring interconnecting the motor ring and the mounting ring, the flex ring disposed about a longitudinal axis of the torque transducer that extends through the motor ring, mounting ring, and the flex ring, the flex ring including:
a first member extending in a direction parallel to the longitudinal axis from a first portion fixed to the motor ring to a second portion fixed to the mounting ring; and
an active strain gauge positioned on the first member between the first and second portions, the active strain gauge configured to measure flexation of the first member in response to the first portion moving relative to the second portion.

16. The torque transducer according to claim 15, wherein the flex ring includes a second member extending in a direction parallel to the longitudinal axis between the motor ring and the mounting ring, the second member configured to flex relatively less than the first member.

17. The torque transducer according to claim 15, wherein the flex ring includes a calibration strain gauge, the calibration strain gauge positioned on a region of the flex ring configured to minimize flexation, the calibration strain gauge configured to account for environmental strain.

18. The torque transducer according to claim 17, wherein the calibration strain gauge is disposed on the first member adjacent the motor ring.

19. The torque transducer according to claim 17, wherein the calibration strain gauge is disposed on the first member adjacent the mounting ring.

20. The torque transducer according to claim 15, wherein the active strain gauge is oriented to measure strain in a direction transverse to the longitudinal axis.

* * * * *